United States Patent
Christensen et al.

(10) Patent No.: US 11,160,288 B2
(45) Date of Patent: Nov. 2, 2021

(54) USE OF GLUCOSE DEFICIENT STREPTOCOCCUS THERMOPHILES STRAINS IN A PROCESS FOR PRODUCING FERMENTED MILK PRODUCTS

(71) Applicant: Chr. Hansen A/S, Hoersholm (DK)

(72) Inventors: Nanna Christensen, Copenhagen S (DK); Tina Hoegholm, Kokkedal (DK); Pia Frost Jensen, Birkeroed (DK); Claus Svane, Rungsted Kyst (DK)

(73) Assignee: CHR. HANSEN A/S, Hoersholm (DK)

( * ) Notice: Subject to any disclaimer, the term of this patent is extended or adjusted under 35 U.S.C. 154(b) by 429 days.

(21) Appl. No.: 16/089,350

(22) PCT Filed: Mar. 24, 2017

(86) PCT No.: PCT/EP2017/057083
§ 371 (c)(1),
(2) Date: Sep. 27, 2018

(87) PCT Pub. No.: WO2017/167660
PCT Pub. Date: Oct. 5, 2017

(65) Prior Publication Data
US 2020/0305452 A1 Oct. 1, 2020

(30) Foreign Application Priority Data
Mar. 31, 2016 (EP) ..................... 16163186

(51) Int. Cl.
*A23C 9/123* (2006.01)
*C12N 1/20* (2006.01)
*C12N 9/12* (2006.01)
*C12R 1/23* (2006.01)
*C12R 1/46* (2006.01)

(52) U.S. Cl.
CPC .......... *A23C 9/1234* (2013.01); *A23C 9/1238* (2013.01); *C12N 1/20* (2013.01); *C12N 9/1205* (2013.01); *A23Y 2220/15* (2013.01); *A23Y 2220/29* (2013.01); *A23Y 2240/75* (2013.01); *C12N 1/205* (2021.05); *C12R 2001/23* (2021.05); *C12R 2001/46* (2021.05)

(58) Field of Classification Search
CPC ...... A23C 9/1234; A23C 9/1238; C12N 1/20; C12N 9/1205; A23Y 2220/15; A23Y 2220/29; A23Y 2240/75; C12R 1/23; C12R 1/46
USPC .......................................................... 426/43
See application file for complete search history.

(56) References Cited

U.S. PATENT DOCUMENTS

2015/0086675 A1* 3/2015 Johansen ............. C12N 15/746
426/43

FOREIGN PATENT DOCUMENTS

EP 2957180 A1 12/2015
WO WO-2011/026863 A1 3/2011

OTHER PUBLICATIONS

Cochu et al., "Genetic and Biochemical Characterization of the Phosphoenolpyruvate: Glucose/Mannose Phosphotransferase System of *Streptococcus thermophilus*," Applied and Environmental Microbiology, vol. 69, No. 9, pp. 5423-5432 (Sep. 2003).
Høier et al., "The Production, Application and Action of Lactic Cheese Starter Cultures," Technology of Cheesemaking, Second Edition, pp. 166-192 (2010).
Pool et al., "Natural sweeting of food products by engineering *Lactococcus lactis* for glucose production," Metabolic Engineering, vol. 8, pp. 456-465 (May 2006).
Sieuwerts et al., "Unraveling Microbial Interctions in Food Fermentations: from Classical to Genomics Approaches," Applied and Environmental Microbiology, vol. 74, No. 16, pp. 4997-5007 (Aug. 2008).

* cited by examiner

*Primary Examiner* — Brent T O'Hern
(74) *Attorney, Agent, or Firm* — Foley & Lardner LLP

(57) ABSTRACT

The invention relates to the use of a *Streptococcus thermophilus* strain with a deficiency in glucose metabolism for improving growth of a *Lactobacillus* strain in a process for producing a fermented milk product.

12 Claims, No Drawings

USE OF GLUCOSE DEFICIENT *STREPTOCOCCUS THERMOPHILES* STRAINS IN A PROCESS FOR PRODUCING FERMENTED MILK PRODUCTS

CROSS-REFERENCE TO RELATED APPLICATIONS

The present application is the U.S. National Stage of International Application PCT/EP2017/057083, filed Mar. 24, 2017, and claims priority to European Patent Application No. 16163186.6, filed Mar. 31, 2016.

FIELD OF INVENTION

The present invention relates to the use of *Streptococcus thermophilus* bacteria strains with a deficiency in the glucose metabolism in combination with a *Lactobacillus* strain in a process for producing a fermented milk product.

BACKGROUND OF THE INVENTION

*Streptococcus thermophilus* is one of the most widely used lactic acid bacteria for commercial thermophilic milk fermentation where the organism is normally used as part of a mixed starter culture, the other component being a *Lactobacillus* sp., e.g. *Lactobacillus delbrueckii* subsp. *bulgaricus* for yogurt or *Lactobacillus helveticus* for Swiss-type cheese.

EP-A1-2 957 180 in one embodiment discloses a method of producing a fermented milk product using a combination of a glucose-deficient starter culture and a conventional lactase with an object of reducing content of lactose and the level of post-acidification in the fermented milk product.

WO2013/160413 discloses a galactose-fermenting *Streptococcus thermophilus* strain, wherein the strain carries a mutation in the DNA sequence of the glcK gene encoding a glucokinase protein, wherein the mutation inactivates the glucokinase protein or has a negative effect on expression of the gene. In a specific embodiment the *Streptococcus thermophilus* strain also carries a mutation that reduces the transport of glucose into the cell, e.g. a mutation in a gene encoding a component of a glucose transporter, wherein the mutation inactivates the glucose transporter or has a negative effect on expression of the gene. WO2013/160413 also discloses glucose-deficient *Lactobacillus delbrueckii* subsp. *bulgaricus* strains. When used in a process for producing a fermented milk product the *Streptococcus thermophilus* strains excrete glucose to provide fermented milk products with a natural (inner) sweetness without extra calories, increased sweetness and decreased levels of lactose. Sieuwerts et al., Applied and Environmental Microbiology, August 2008, p. 4997-5007, discloses a review study of microbial interactions in yogurt fermentation and teaches that when the species *Lactobacillus delbrueckii* subsp. *bulgaricus* and *Streptococcus thermophilus* are grown in co-culture, the growth of both species are stimulated. Also, Sieuwerts teaches that *Streptococcus thermophilus* provides *Lactobacillus delbrueckii* subsp. *bulgaricus* with growth stimulating factors, such as formic acid, pyruvic acid and folic acid.

The legal definition of yogurt in many countries requires *Streptococcus thermophilus* alongside *Lactobacillus delbrueckii* subsp. *bulgaricus*. Both species generate desirable amounts of acetaldehyde, which in addition to acidity is an important flavor component in yogurt.

In some fermented milk product types containing *Streptococcus thermophilus* alongside a *Lactobacillus* strain it is desired to obtain a high level of the *Lactobacillus* strain. Also, in some countries the legal definition of such fermented milk products types requires that the *Lactobacillus* strain is present in the product in a level of above 1.0E06 CFU/ml. For such fermented milk products it is a general technical problem that the level of *Lactobacillus* cells obtained at the completion of the fermentation is not as high as is desired. The present invention relates to production of a fermented milk product using *Streptococcus thermophilus* along-side a *Lactobacillus* strain, wherein an increased level of *Lactobacillus* cells may be obtained at the completion of the fermentation.

SUMMARY OF INVENTION

The present invention is directed to the use of a *Streptococcus thermophilus* strain with a deficiency in glucose metabolism for improving growth of a *Lactobacillus* strain in a process for producing a fermented milk product.

The present invention is based on the surprising experimental finding that *Streptococcus thermophilus* strains with a deficiency in glucose metabolism are capable of boosting the growth of lactic acid bacteria strains of the genus *Lactobacillus*. Thus, the use of the invention has provided a possibility of obtaining an increased level of *Lactobacillus* cells at the completion of the fermentation or alternatively using a starter culture blend with a reduced amount of *Lactobacillus* bacteria cells.

Furthermore, when used in a process for producing a fermented milk product *Streptococcus thermophilus* strains with a deficiency in glucose metabolism have the ability to excrete glucose to provide fermented milk products with a natural (inner) sweetness without extra calories, increased sweetness and decreased levels of lactose. Thus, in accordance with the present invention it is possible to produce fermented milk products with a combination of an increased level of *Lactobacillus* bacteria cells and an increased level of natural sweetness.

The present invention further relates to a composition comprising a *Streptococcus thermophilus* strain with a deficiency in glucose metabolism and a *Lactobacillus* strain, wherein the ratio of CFU/g of the *Streptococcus thermophilus* strain to CFU/g of the *Lactobacillus* strain is at least 50.

Furthermore, the present invention relates to a process for producing a fermented milk product comprising inoculating and fermenting a milk substrate with the composition of the invention.

DETAILED DISCLOSURE OF THE INVENTION

Definitions

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures. DVS cultures are intended for direct inoculation into a fermentation vessel or vat for the production of a dairy product, such as a fermented milk product. Such cultures are in general referred to as "starter cultures" or "starters".

The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited here-in. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

A bacterial "strain" as used herein refers to a bacterium which remains genetically unchanged when grown or multiplied. A multiplicity of identical bacteria are included.

The term "galactose-fermenting *Streptococcus thermophilus* strains" as used herein refers to *Streptococcus thermophilus* strains which are capable of growth on/in M17 medium+2% galactose. The galactose-fermenting *Streptococcus thermophilus* strains are defined herein as *Streptococcus thermophilus* strains which lower the pH of M17 broth containing 2% galactose as sole carbohydrate to 5.5 or lower when inoculated from an overnight culture at 1% and incubated for 24 hours at 37° C.

The term "the mutation inactivates the glucokinase protein" as used herein refers to a mutation which results in an "inactivated glucokinase protein", a glucokinase protein which, if present in a cell, is not able to exert its normal function as well as mutations which prevent the formation of the glucokinase protein or result in degradation of the glucokinase protein. In particular, an inactivated glucokinase protein is a protein which compared to a functional glucokinase protein is not able to facilitate phosphorylation of glucose to glucose-6-phosphate or facilitates phosphorylation of glucose to glucose-6-phosphate at a significantly reduced rate. The gene encoding such an inactivated glucokinase protein compared to the gene encoding a functional glucokinase protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

The term "functional glucokinase protein" as used herein refers to a glucokinase protein which, if present in a cell, facilitates phosphorylation of glucose to glucose-6-phosphate. In particular, a functional glucokinase protein may be encoded by a gene comprising an ORF which has a sequence corresponding to position 1-966 in SEQ ID NO. 1 or a sequence which has at least 85% identity, such as at least 90% identity, such as at least 95% identity, such as at least 98% identity, such as at least 99% identity, to the sequence corresponding to position 1-966 of SEQ ID NO. 1.

The percent identity of two sequences can be determined by using mathematical algorithms, such as the algorithm of Karlin and Altschul (1990. Proc. Natl. Acad. Sci. USA 87; 2264), the modified algorithm described in Karlin and Altschul (1993. Proc. Natl. Acad. Sci. USA 90; 5873-5877); the algorithm of Myers and Miller (1988. CABIOS 4; 11-17); the algorithm of Needleman and Wunsch (1970. J. Mol. Biol. 48; 443-453); and algorithm of Pearson and Lipman (1988. Proc. Natl. Acad. Sci. USA 85; 2444-2448). Computer software for the determination of nucleic acid or amino acid sequence identity based on these mathematical algorithms is also available. For example, the comparison of nucleotide sequences can be performed with the BLASTN program, score=100, wordlength=12. The comparison of amino acid sequences can be performed with the BLASTX program, score=50, wordlength=3. For the remaining parameters of the BLAST programs, the default parameters can be used.

A "mutant bacterium" or a "mutant strain" as used herein refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with chemical mutagens, UV- or gamma radiation etc. In contrast, a "spontaneous mutant" or "naturally occurring mutant" has not been mutagenized by man. Mutant bacteria are herein, non-GMO (non-genetically modified organism), i.e. not modified by recombinant DNA technology.

"Wild type strain" refers to the non-mutated form of a bacterium, as found in nature.

Terms such as "strains with a sweetening property", "strains which can provide a desirable accumulation of glucose in the fermented milk product" and "strains with enhanced properties for natural sweetening of food products" are used interchangeably herein to characterize an advantageous aspect of using the strains of the present invention in fermentation of milk products.

The term "resistant to 2-deoxyglucose" herein in relation to *Streptococcus thermophilus* is defined by that a particular mutated bacterial strain has the ability to grow to a colony when streaked on a plate of M17 medium containing 20 mM 2-deoxyglucose after incubation at 40° C. for 20 hours. The presence of 2-deoxygluxcose in the culture medium will prevent the growth of non-mutated strains while the growth of the mutated strains is not affected or not affected significantly. Non-mutated strains which can be used as sensitive reference strains in the assessment of resistance preferably include the strains CHCC14994 and CHCC11976.

The term "a mutation that reduces the transport of glucose into the cell" as used herein refers to a mutation in a gene encoding a protein involved in transport of glucose which results in an accumulation of glucose in the environment of the cell.

The level of glucose in the culture medium of a *Streptococcus thermophilus* strain can readily be measured by methods known to the skilled person.

The term "the mutation inactivates the glucose transporter" as used herein refers to a mutation which results in an "inactivated glucose transporter", a glucose transporter protein which, if present in a cell, is not able to exert its normal function as well as mutations which prevent the formation of the glucose transporter protein or result in degradation of the glucose transporter protein.

The term "functional glucose transporter protein" as used herein refers to a glucose transporter protein which, if present in a cell, facilitates transport of glucose over a plasma membrane.

In the present context, the term "strains derived therefrom" should be understood as strains derived, or strains which can be derived from a strain (or their mother strain)

of the invention by means of e.g. genetic engineering, radiation and/or chemical treatment. The "strains derived therefrom" can also be spontaneously occurring mutants. It is preferred that the "strains derived therefrom" are functionally equivalent mutants, e.g. mutants that have substantially the same, or improved, properties (e.g. regarding excretion of glucose) as their mother strain. Such "strains derived therefrom" are part of the present invention. Especially, the term "strains derived therefrom" refers to strains obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood as one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

The term "resistant to 2-deoxyglucose" in relation to a *Lactobacillus delbrueckii* subsp. *bulgaricus* strain is defined by that a particular bacterial strain has the ability to grow to a colony after incubation at 40° C. for 20 hours when streaked on a plate of MRS-IM medium containing 2% lactose and 20 mM 2-deoxyglucose. The presence of 2-deoxyglucose in the culture medium will prevent the growth of non-resistant strains while the growth of resistant strains is not affected or not affected significantly. Non-resistant *Lactobacillus delbrueckii* subsp. *bulgaricus* strains which can be used as sensitive reference strains in the assessment of resistance include the *Lactobacillus delbrueckii* subsp. *bulgaricus* strains CHCC759 that was deposited at Deutsche Sammlung von Mikroorganismen und Zellkulturen (DSMZ) under the accession no. DSM 26419 and CHCC10019, that was deposited Deutsche Sammlung von Mikroorganismen und Zellkulturen (DSMZ) under the accession no. DSM 19252.

The term "glucose-deficient" is used in the context of the present invention to characterize LAB which either partially or completely have lost the ability to use glucose as a source for cell growth or maintaining cell viability. A respective deficiency in glucose metabolism can for example be caused by a mutation in a gene inhibiting or inactivating expression or activity of the glucokinase protein or the glucose transporter protein. LAB with a deficiency in glucose metabolism can be characterized as increasing the glucose concentration in a culture medium, when grown on lactose as carbohydrate source. The increase of glucose is caused by glucose secretion of the glucose deficient LABs. Increase of glucose concentration in a culture medium can be determined by HPLC analysis, for example using a Dionex CarboPac PA 20 3*150 mm column (Thermo Fisher Scientific, product number 060142).

The term "glucose-positive" is used in the context of the present invention to characterize LAB which either partially or completely have maintained the ability to use glucose as a source for cell growth or maintaining cell viability.

The term "genus" means genus as defined on the following website: http://www.ncbi.nlm.nih.gov/Taxonomy/Browser/wwwtax.cgi In connection with strains of the genus *Lactobacillus*, the term "CFU" means colony forming units as determined by growth (forming a colony) on an MRS agar plate incubated at anaerobic conditions at 37° C. for 3 days. The MRS agar has the following composition (g/l):
Bacto Proteose Peptone No. 3: 10.0
Bacto Beef extract: 10.0
Bacto Yeast extract: 5.0
Dextrose: 20.0
Sorbitan Monooleate Complex: 1.0
Ammonium Citrate: 2.0
Sodium Acetate: 5.0
Magnesium Sulfate: 0.1
Manganese Sulfate: 0.05
Potassium Phosphate Dibasis: 2.0
Bacto Agar: 15.0
Milli-Q water: 1000 ml.
pH is adjusted to 5.4 or 6.5: pH is adjusted to 6.5 for *L. rhamnosus, L. casei* and *L. paracasei*. For all other *Lactobacillus* species the pH is adjusted to 5.4. In particular, pH is adjusted to 5.4 for *L. delbrueckii* subsp. *bulgaricus; L. acidophilus* and *L. helveticus*. pH is adjusted to 6.5 for *L. rhamnosus, L. casei* and *L. paracasei*.

In connection with *Streptococcus thermophilus*, the term "CFU" means colony forming units as determined by growth (forming a colony) on an M17 agar plate incubated at aerobic conditions at 37° C. for 3 days. The M17 agar has the following composition (g/l):
Tryptone: 2.5 g
Peptic digest of meat: 2.5 g
Papaic digest of soybean meal: 5.0 g
Yeast extract: 2.5 g
Meat extract: 5.0 g
Lactose: 5.0 g
Sodium-glycero-phosphate: 19.0 g
Magnesium sulphate, 7 $H_2O$: 0.25 g
Ascorbic acid: 0.5 g
Agar: 15.0 g
Milli-Q water: 1000 ml.
pH is adjusted to final pH 7.1±0.2 (25° C.)

The expression "ratio of CFU/g of the *Streptococcus thermophilus* strain to CFU/g of the *Lactobacillus* strain" means the cell count of the *Streptococcus thermophilus* strain in CFU/g contained in the composition divided by the cell count of the *Lactobacillus* strain in CFU/g contained in the composition. If more than one *Streptococcus thermophilus* strain is present in the composition, the said cell count is the sum of all *Streptococcus thermophilus* bacteria present. If more than one *Lactobacillus* strain is present in the composition, the said cell count is the sum of all *Lactobacillus* bacteria present.

The term "X.YEZZ" means $X.Y \times 10^{ZZ}$.

*Streptococcus thermophilus* Strain in the use According to the Invention

In a particular embodiment of the use of the invention, the *Streptococcus thermophilus* strain is galactose-fermenting and carries a mutation in the DNA sequence of the glcK gene encoding a glucokinase protein, wherein the mutation inactivates the glucokinase protein or has a negative effect on expression of the gene. Methods for measuring the level of glucokinase activity or the level of expression of the glucokinase gene are readily known (Porter et al. (1982) Biochim. Biophys. Acta, 709; 178-186) and include enzyme assays with commercially available kits and transcriptomics or quantitative PCR using materials which are readily available.

In preferred embodiments the mutation reduces the activity (the rate of phosphorylation of glucose to glucose-6- phosphate) of the glucokinase protein with at least 50%, such as at least 60%, such as at least 70%, such as at least 80%, such as at least 90%.

The glucokinase activity can be determined by the glucokinase enzymatic assays as described by Pool et al. (2006. Metabolic Engineering 8; 456-464).

Galactose-fermenting strains may be obtained by the method described in WO 2011/026863.

In a particular embodiment of the use of the invention, the *Streptococcus thermophilus* strain carries a mutation that reduces the transport of glucose into the cell. In a specific embodiment, the *Streptococcus thermophilus* strain carries a mutation in a gene encoding a component of a glucose transporter, wherein the mutation inactivates the glucose transporter or has a negative effect on expression of the gene. In a more specific embodiment, the *Streptococcus thermophilus* strain carries a mutation in the DNA sequence of the manM gene encoding the $IIC^{Man}$ protein of the glucose/mannose phosphotransferase system, wherein the mutation inactivates the $IIC^{Man}$ an protein or has a negative effect on expression of the gene. In another specific embodiment of the invention the *Streptococcus thermophilus* strain of the invention carries a mutation in the DNA sequence of the manN gene encoding the $IID^{Man}$ an protein of the glucose/mannose phosphotransferase system, wherein the mutation inactivates the $IID^{Man}$ an protein or has a negative effect on expression of the gene.

In preferred embodiments the mutation reduces the transport of glucose into the cell with at least 50%, such as at least 60%, such as at least 70%, such as at least 80%, such as at least 90%.

The transport of glucose into the cell can be determined by the glucose uptake assay as described by Cochu et al. (2003. Appl Environ Microbiol 69(9); 5423-5432).

Preferably, the *Streptococcus thermophilus* strain carries a mutation in a gene encoding a component of a glucose transporter, wherein the mutation inactivates the glucose transporter protein or has a negative effect on expression of the gene.

The component may be any component of a glucose transporter protein which is critical for the transport of glucose. E.g., it is contemplated that inactivation of any component of the glucose/mannose phosphotransferase system in *Streptococcus thermophilus* will result in inactivation of the glucose transporter function.

In particular, an inactivated glucose transporter protein is a protein which compared to a functional glucose transporter protein is not able to facilitate transport of glucose over a plasma membrane or facilitates transport of glucose over a plasma membrane at a significantly reduced rate. The gene encoding such an inactivated glucose transporter protein compared to the gene encoding a functional glucose transporter protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of transport of glucose) of the glucose transporter protein by at least 50%, such as at least 60%, such as at least 70%, such as at least 80%, such as at least 90%.

The glucose transporter activity can be determined by the glucose uptake assay as described by Cochu et al. (2003. Appl Environ Microbiol 69(9); 5423-5432).

In a particular embodiment of the use of the invention, the *Streptococcus thermophilus* strain increases the amount of glucose in 9.5% B-milk to at least 5 mg/ml when inoculated into the 9.5% B-milk at a concentration of 1.0E06-1.0E07 CFU/ml and grown at 40° C. for 20 hours.

In a particular embodiment of the use of the invention, the *Streptococcus thermophilus* strain increases the amount of glucose in 9.5% B-milk with 0.05% sucrose to at least 5 mg/ml when inoculated into the 9.5% B-milk with 0.05% sucrose at a concentration of 1.0E06-1.0E07 CFU/ml and grown at 40° C. for 20 hours.

In the present context, 9.5% B-milk is heat-treated milk made with reconstituted low fat skim milk powder to a level of dry matter of 9.5% and pasteurized at 99° C. for 30 min. followed by cooling to 40° C.

In more preferred embodiments of the invention the mutant strain leads to an increase in the amount of glucose to at least 6 mg/mL, such as at least 7 mg/mL, such as at least 8 mg/mL, such as at least 9 mg/ml, such as at least 10 mg/ml, such as at least 11 mg/ml, such as at least 12 mg/ml, such as at least 13 mg/ml, such as at least 14 mg/ml, such as at least 15 mg/ml, such as at least 20 mg/ml, such as at least 25 mg/ml.

In a particular embodiment of the use of the invention, the *Streptococcus thermophilus* strain is selected from the group consisting of the *Streptococcus thermophilus* CHCC15757 strain that was deposited at Deutsche Sammlung von Mikroorganismen and Zellkulturen under accession No. DSM 25850, the *Streptococcus thermophilus* CHCC15887 strain that was deposited at Deutsche Sammlung von Mikroorganismen und Zellkulturen under accession No. DSM 25851, the *Streptococcus thermophilus* CHCC16404 strain that was deposited at Deutsche Sammlung von Mikroorganismen und Zellkulturen under accession No. DSM 26722, the *Streptococcus thermophilus* CHCC16731 which was deposited with Deutsche Sammlung von Mikroorganismen und Zellkulturen under the accession no. DSM 28889, the *Streptococcus thermophilus* CHCC19216 which was deposited with Deutsche Sammlung von Mikroorganismen und Zellkulturen under the accession no. DSM 32227 and a mutant strain derived therefrom, wherein the mutant strain is obtained by using one of the deposited strains as starting material, and wherein the mutant has retained or further improved the lactose fermenting property and/or the glucose secreting property of said deposited strain.

In a much preferred embodiment of the present invention the mutant strain is a naturally occurring mutant or an induced mutant.

In another embodiment of the invention the mutant strain of *Streptococcus thermophilus* is resistant to 2-deoxyglucose.

*Lactobacillus* Strain in the Use According to the Invention

The *Lactobacillus* bacteria strain of the invention may be any bacteria strain of the genus *Lactobacillus*. In a particular embodiment the *Lactobacillus* strain is selected from the group consisting of *Lactobacillus delbrueckii, Lactobacillus delbrueckii* subsp. *bulgaricus, Lactobacillus delbrueckii* subsp. *lactis, Lactobacillus paracasei, Lactobacillus casei, Lactobacillus rhamnosus, Lactobacillus fermentum, Lactobacillus plantarum, Lactobacillus helveticus, Lactobacillus acidophilus*. In a preferred embodiment of the invention the *Lactobacillus* strain is selected from the group consisting of *Lactobacillus delbrueckii* subsp. *bulgaricus, Lactobacillus paracasei* and *Lactobacillus acidophilus*.

In a particular embodiment the *Lactobacillus* bacteria strain of the invention is *Lactobacillus delbrueckii* subsp. *bulgaricus. Lactobacillus delbrueckii* subsp. *bulgaricus* is a lactic acid bacterium which is frequently employed for commercial milk fermentation where the organism is normally used as part of a mixed starter culture.

In one embodiment of the invention, the *Lactobacillus* bacteria strain of the invention is glucose-deficient. In an alternative embodiment of the invention the *Lactobacillus* bacteria strain of the invention is glucose-positive.

In particular, the *Lactobacillus delbrueckii* subsp. *bulgaricus* strain of the invention is a strain, which is resistant to 2-deoxyglucose. In a particular embodiment of the invention the *Lactobacillus* strain is *Lactobacillus delbrueckii* subsp. *bulgaricus* strain, wherein the strain is resistant to 2-deoxyglucose and wherein the strain increases the amount of glucose in 9.5% B-milk to at least 5 mg/ml when inoculated into the 9.5% B-milk at a concentration of 1.0E06-1.0E07 CFU/ml and grown at 40° C. for at least 20 hours.

In a particular embodiment of the invention, the *Lactobacillus delbrueckii* subsp. *bulgaricus* strain is selected from the group consisting of the *Lactobacillus delbrueckii* subsp. *bulgaricus* strain CHCC16159 that was deposited at Deutsche Sammlung von Mikroorganismen und Zellkulturen (DSMZ) under accession no. DSM26420, the *Lactobacillus delbrueckii* subsp. *bulgaricus* strain CHCC16160 that was deposited at Deutsche Sammlung von Mikroorganismen und Zellkulturen (DSMZ) under accession no. DSM26421 and a mutant strain derived therefrom, wherein the mutant strain is obtained by using one of the deposited strains as starting material, and wherein the mutant has retained or further improved the lactose fermenting property and/or the glucose secreting property of said deposited strain.

In another particular embodiment of the invention, the *Lactobacillus delbrueckii* subsp. *bulgaricus* strain is selected from the group consisting of the *Lactobacillus delbrueckii* subsp. *bulgaricus* strain CHCC4351 that was deposited at Deutsche Sammlung von Mikroorganismen und Zellkulturen (DSMZ) under accession no. DSM22586 and a mutant strain derived therefrom, wherein the mutant strain is obtained by using one of the deposited strains as starting material.

In a particular embodiment of the invention, the *Lactobacillus paracasei* strain is selected from the group consisting of the strain CHCC2115 that was deposited with DSMZ-Deutsche Sammlung von Mikroorganismen und Zellkulturen GmbH under the accession no. DSM 19465, and a mutant strain derived therefrom, wherein the mutant strain is obtained by using one of the deposited strains as starting material.

In a particular embodiment of the invention, the *Lactobacillus acidophilus* strain is selected from the group consisting of the strain CHCC2169 that has been deposited as DSM13241 at Deutsche Sammlung von Mikroorganismen and Zellkulturen GmbH, and a mutant strain derived therefrom, wherein the mutant strain is obtained by using one of the deposited strains as starting material.

Fermented Milk Products Produced in the Use According to the Invention

The term "milk" is to be understood as the lacteal secretion obtained by milking any mammal, such as a cow, a sheep, a goat, a buffalo or a camel. In a preferred embodiment, the milk is cow's milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the metabolism of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

The term "fermented milk product" as used herein refers to a food or feed product wherein the preparation of the food or feed product involves fermentation of a milk substrate with a lactic acid bacteria. "Fermented milk product" as used herein includes but is not limited to products such as yogurt and cheese.

Examples of cheeses which are prepared by fermentation with *Streptococcus thermophilus* and *Lactobacillus delbrueckii* subsp. *bulgaricus* include Mozzarella and pizza cheese (Høier et al. (2010) in The Technology of Cheesemaking, $2^{nd}$ Ed. Blackwll Publishing, Oxford; 166-192).

Preferably, the fermented milk product is a yogurt.

In the present context, a yogurt starter culture is a bacterial culture which comprises at least one *Lactobacillus delbrueckii* subsp *bulgaricus* strain and at least one *Streptococcus thermophilus* strain. In accordance herewith, the term "yogurt" refers to a fermented milk product obtainable by inoculating and fermenting milk with a composition comprising a *Lactobacillus delbrueckii* subsp *bulgaricus* strain and a *Streptococcus thermophilus* strain.

Use According to the Invention

In one embodiment of the use of a *Streptococcus thermophilus* strain with a deficiency in glucose metabolism for improving growth of a *Lactobacillus* strain in a process for producing a fermented milk product, the ratio of the *Streptococcus thermophilus* strain to the *Lactobacillus* strain is selected to be at a conventional level, and hence an increased level of the *Lactobacillus* strain is obtained in the fermented milk product. In particular, the ratio of CFU/g of the *Streptococcus thermophilus* strain to CFU/g of the *Lactobacillus* strain is from 10 to 500, preferably from 50 to 400, more preferably from 80 to 300, and most preferably from 100 to 200.

In a second embodiment of the use of a *Streptococcus thermophilus* strain with a deficiency in glucose metabolism for improving growth of a *Lactobacillus* strain in a process for producing a fermented milk product, the ratio of the *Streptococcus thermophilus* strain to the *Lactobacillus* strain is selected to be at a reduced level, and hence a conventional level of the *Lactobacillus* strain is obtained in the fermented milk product. In particular, at the start of the fermentation the ratio of CFU/g of the *Streptococcus thermophilus* strain to CFU/g of the *Lactobacillus* strain is at least 50, preferably at least 80, more preferably at least 100, more preferably at least 150, more preferably at least 200, more preferably at least 250, more preferably at least 300, more preferably at least 350, more preferably at least 400, more preferably at least 450, more preferably at least 500, more preferably at least 550, more preferably at least 600, more preferably at least 650, more preferably at least 700, more preferably at least 750, more preferably at least 800, more preferably at least 850, more preferably at least 900, and most preferably at least 950. In this case, the ratio of CFU/g of the *Streptococcus thermophilus* strain to CFU/g of the *Lactobacillus* strain is below 2000, more preferably below 1800, more preferably below 1600, more preferably below 1400, more preferably below 1200, and most preferably below 1000.

In a particular embodiment of the use of the invention, the *Streptococcus thermophilus* strain increases the amount of the *Lactobacillus* strain to at least 5.0E06 CFU/g in the fermented milk product at the end of fermentation when inoculated into a milk substrate at a concentration of 1.0E07-1.0E08 CFU/g in the milk substrate and grown at 43° C. until the pH reaches 4.55, wherein the milk substrate is a mixture of fresh skimmed milk with a fat content of 0.1%, fresh semi-skimmed milk with a fat content of 1.5%, and skimmed milk powder, and wherein the milk substrate contains 4.7% protein and 1.0% fat, and 0.05% sucrose.

Composition of the Invention

The present invention further relates to a composition comprising a *Streptococcus thermophilus* strain with a deficiency in glucose metabolism and a *Lactobacillus* strain, wherein the ratio of CFU/g of the *Streptococcus thermophilus* strain to CFU/g of the *Lactobacillus* strain is at least 50.

The composition of the invention is based on the surprising experimental finding that *Streptococcus thermophilus* strains with a deficiency in glucose metabolism is capable of boosting the growth of lactic acid bacteria strains of the genus *Lactobacillus*, and that therefore it is possible to carry out milk fermentations with a starter culture blend having a reduced level of the *Lactobacillus* strain in relation to the *Streptococcus thermophilus* strain and still obtain an acceptable level of the *Lactobacillus* strain at the completion of the fermentation.

In a particular embodiment of the composition of the invention, the ratio of CFU/g of the *Streptococcus thermophilus* strain to CFU/g of the *Lactobacillus* strain is at least 80, preferably at least 100, more preferably at least 150, more preferably at least 200, more preferably at least 250, more preferably at least 300, more preferably at least 350, more preferably at least 400, more preferably at least 450, more preferably at least 500, more preferably at least 550, more preferably at least 600, more preferably at least 650, more preferably at least 700, more preferably at least 750, more preferably at least 800, more preferably at least 850, more preferably at least 900, and most preferably at least 950.

In a particular embodiment of the composition of the invention, the ratio of CFU/g of the *Streptococcus thermophilus* strain to CFU/g of the *Lactobacillus* strain is below 2000, more preferably below 1800, more preferably below 1600, more preferably below 1400, more preferably below 1200, and most preferably below 1000.

In a particular embodiment, the composition of the invention comprises from 1.0E04 to 1.0E12 CFU/g of the *Streptococcus thermophilus* strain, such as from 1.0E05 to 1.0E11 CFU/g, such as from 1.0E06 to 1.0E10 CFU/g, or such as from 1.0E07 to 1.0E09 CFU/g of the *Streptococcus thermophilus* strain.

In particular, the *Streptococcus thermophilus* strain of the composition of the invention is a *Streptococcus thermophilus* strain as described above in relation to the use of the invention. In particular, the *Lactobacillus* strain of the composition of the invention is a *Lactobacillus* strain as described above in relation to the use of the invention.

In a preferred composition of the present invention, the *Streptococcus thermophilus* strain is selected from the group consisting of the *Streptococcus thermophilus* CHCC15757 strain that was deposited at Deutsche Sammlung von Mikroorganismen und Zellkulturen under accession No. DSM 25850, the *Streptococcus thermophilus* CHCC15887 strain that was deposited at Deutsche Sammlung von Mikroorganismen und Zellkulturen under accession No. DSM 25851, the *Streptococcus thermophilus* CHCC16404 strain that was deposited at Deutsche Sammlung von Mikroorganismen und Zellkulturen under accession No. DSM 26722, the *Streptococcus thermophilus* CHCC16731 which was deposited with Deutsche Sammlung von Mikroorganismen und Zellkulturen under the accession no. DSM 28889, the *Streptococcus thermophilus* CHCC19216 which was deposited with Deutsche Sammlung von Mikroorganismen und Zellkulturen under the accession no. DSM 32227 and a mutant strain derived therefrom, wherein the mutant strain is obtained by using one of the deposited strains as starting material, and wherein the mutant has retained or further improved the lactose fermenting property and/or the glucose secreting property of said deposited strain.

In one embodiment of the invention, the *Lactobacillus* bacteria strain of the invention is glucose-deficient. In an alternative embodiment of the invention the *Lactobacillus* bacteria strain of the invention is glucose-positive.

In a preferred composition of the present invention, the *Lactobacillus delbrueckii* subsp. *bulgaricus* strain is selected from the group consisting of the *Lactobacillus delbrueckii* subsp. *bulgaricus* strain CHCC16159 that was deposited at Deutsche Sammlung von Mikroorganismen und Zellkulturen under accession No. DSM 26420, the *Lactobacillus delbrueckii* subsp. *bulgaricus* strain CHCC16160 that was deposited at Deutsche Sammlung von Mikroorganismen und Zellkulturen under accession No. DSM 26421, and a mutant strain derived therefrom, wherein the mutant strain is obtained by using one of the deposited strains as starting material, and wherein the mutant has retained or further improved the lactose fermenting property and/or the glucose secreting property of said deposited strain.

In another particular embodiment of the composition of the invention, the *Lactobacillus delbrueckii* subsp. *bulgaricus* strain is selected from the group consisting of the *Lactobacillus delbrueckii* subsp. *bulgaricus* strain CHCC4351 that was deposited at Deutsche Sammlung von Mikroorganismen und Zellkulturen (DSMZ) under accession no. DSM22586 and a mutant strain derived therefrom, wherein the mutant strain is obtained by using one of the deposited strains as starting material, and wherein the mutant has retained or further improved the glucose fermenting property of said deposited strain.

*Lactobacillus delbrueckii* subsp. *bulgaricus*, *Streptococcus thermophilus* and other lactic acid bacteria are commonly used as starter cultures serving a technological purpose in the production of various foods, such as in the dairy industry, such as for fermented milk products. Thus, in another preferred embodiment the composition is suitable as a starter culture.

Starter cultures may be provided as frozen or dried starter cultures in addition to liquid starter cultures. Thus, in yet another preferred embodiment the composition is in frozen, freeze-dried or liquid form.

As disclosed in WO 2005/003327, it is beneficial to add certain cryoprotective agents to a starter culture. Thus, a starter culture composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds.

Process for Producing a Fermented Milk Product

The present invention further relates to a process for producing a fermented milk product comprising inoculating and fermenting a milk substrate with the composition of the invention.

Embodiments of the present invention are described below, by way of non-limiting examples.

EXAMPLES

Materials and Methods

Agar Medium for Cell Count of *Lactobacillus delbrueckii* subsp. *bulgaricus* Strains CFU was determined by growth (forming a colony) on an MRS agar plate incubated at anaerobic conditions at 37° C. for 3 days. The MRS agar has the following composition (g/l):

Bacto Proteose Peptone No. 3: 10.0
Bacto Beef extract: 10.0
Bacto Yeast extract: 5.0
Dextrose: 20.0
Sorbitan Monooleate Complex: 1.0
Ammonium Citrate: 2.0
Sodium Acetate: 5.0
Magnesium Sulfate: 0.1
Manganese Sulfate: 0.05
Potassium Phosphate Dibasis: 2.0
Bacto Agar: 15.0
Milli-Q water: 1000 ml.
pH is adjusted to 5.4.

Agar Medium for Cell Count of *Streptococcus thermophilus* Strains

For *Streptococcus thermophilus*, the medium used is the M17 medium known to persons skilled in the art. Bacteria were grown at aerobic conditions at 37° C. for 3 days.

The M17 agar medium has the following composition (g/l):

Tryptone: 2.5 g
Peptic digest of meat: 2.5 g
Papaic digest of soybean meal: 5.0 g
Yeast extract: 2.5 g
Meat extract: 5.0 g
Lactose: 5.0 g
Sodium-glycero-phosphate: 19.0 g
Magnesium sulphate, 7 $H_2O$: 0.25 g
Ascorbic acid: 0.5 g
Agar: 15.0 g
Milli-Q water: 1000 ml.
pH is adjusted to final pH 7.1±0.2 (25° C.)

Example 1: Effect of Glucose-Deficient *Streptococcus thermophilus* Strains on the Growth of *Lactobacillus* Strains in Fermentation of Milk A total of 4 different bacteria strain blends each composed of a number of *Streptococcus thermophilus* strains and one *Lactobacillus delbrueckii* subsp. *bulgaricus* strains were tested in process of producing yogurt from a milk substrate in order to determine the effect of glucose-deficient *Streptococcus thermophilus* strains on the growth of *Lactobacillus delbrueckii* subsp. *bulgaricus* strains.

Two blends according to the use of the invention were composed of a mixture of glucose-deficient *Streptococcus thermophilus* strains in combination with either a glucose-deficient *Lactobacillus delbrueckii* subsp. *bulgaricus* strain or a glucose-positive *Lactobacillus delbrueckii* subsp. *bulgaricus* strain. For comparison, 2 blends were composed of a mixture of glucose-positive *Streptococcus thermophilus* strains in combination with either a glucose-deficient *Lactobacillus delbrueckii* subsp. *bulgaricus* strain or a glucose-positive *Lactobacillus delbrueckii* subsp. *bulgaricus* strain. The components and composition of the 4 blends appear from Table 1.

TABLE 1

Composition and growth of blends of *Lactobacillus delbrueckii* subsp. *bulgaricus* and glucose-positive or glucose-deficient *Streptococcus thermophilus*

| Blend components in % by weight (g/g) | Blend 1: Glu(−) St Glu(−) Lb | Blend 2: Glu(−) St Glu(+) Lb | Blend 3: Glu(+) St Glu(−) Lb | Blend 4: Glu(+) St Glu(+) Lb |
|---|---|---|---|---|
| Glu(−) St | 90.91 | 94.44 | | |
| Glu(−) Lb | 9.09 | | 9.09 | |
| Glu(+) St | | | 90.91 | 94.44 |
| Glu(+) Lb | | 5.56 | | 5.56 |
| Ratio of St to Lb | 95.18 | 88.47 | 95.18 | 88.47 |
| Cell count for Lb at end of fermentation (CFU/g) | 5.69E07 | 6.75E08 | 1.20E06 | 1.57E06 |

Glu(−): Glucose-deficient
Glu(+): Glucose-positive
St: *Streptococcus thermophilus*
Lb: *Lactobacillus delbrueckii* subsp. *bulgaricus*

The level of total culture inoculation was 0.018% by weight (g/ml). The milk substrate used was a mixture of fresh skimmed milk (fat 0.1%), fresh semi-skimmed milk (fat 1.5%), skimmed milk powder from Lactalis and ProMilk 802 from Ingredia (Milk Soluble Protein Isolate). The final milk substrate contained 4.7% protein and 1.0% fat, and 0.05% sucrose. The fermentation of the milk was carried out in 200 ml containers at a temperature of 43° C. until an end pH of 4.55 was reached.

Table 1 also lists for each of the Blends 1-4 the ratio of the sum of cell counts for *Streptococcus thermophilus* to the cell count for the *Lactobacillus delbrueckii* subsp. *bulgaricus* at the start of fermentation as well as the cell count (CFU/g) for *Lactobacillus delbrueckii* subsp. *bulgaricus* at the end of fermentation. The results listed in Table 1 are an average of a replicate determination.

The two fermentations using glucose-positive *Streptococcus thermophilus* strains resulted in cell counts of 1.20E06 and 1.57E06 for the glucose-deficient and the glucose-positive *L. delbrueckii* subsp. *bulgaricus*, respectively. Using glucose-deficient *Streptococcus thermophilus* strains increased the level to 5.69E07 and 6.75E08 for the glucose-deficient *L. delbrueckii* subsp. *bulgaricus* and the glucose-positive *L. delbrueckii* subsp. *bulgaricus*, respectively. Thus, the use of glucose-deficient *Streptococcus thermophilus* strains had a significant boosting effect on the growth of both glucose-deficient and glucose-positive *L. delbrueckii* subsp. *bulgaricus*.

Example 2: Effect of Glucose-Deficient *Streptococcus thermophilus* Strains on the Growth of *Lactobacillus* Strains in Fermentation of Milk Using Low Initial *Lactobacillus* Cell Levels Bacteria strain blends in different ratios of a mixture of glucose-deficient *Streptococcus thermophilus* strains to a glucose-positive *Lactobacillus delbrueckii* subsp. *bulgaricus* strain were tested in a process of producing yogurt from a milk substrate in order to determine the effect of glucose-deficient *Streptococcus thermophilus* strains on the growth of *Lactobacillus delbrueckii* subsp. *bulgaricus* strains. The composition of the said blends and the said different ratios appear from Table 2.

The milk substrate used was a mixture of fresh skimmed milk (fat 0.1%), fresh semi-skimmed milk (fat 1.5%), skimmed milk powder from Lactalis and ProMilk 802 from Ingredia (Milk Soluble Protein Isolate). The final milk substrate contained 4.7% protein and 1.0% fat, and 0.05% sucrose. The fermentation of the milk was carried out in 200 ml containers at a temperature of 43° C. until an end pH of 4.55 was reached.

TABLE 2

Growth of *Lactobacillus delbrueckii* subsp. *bulgaricus* in the presence of glucose-deficient *Streptococcus thermophilus* at different ratios

| | Culture composition | | | Lb cell count after fermentation | |
|---|---|---|---|---|---|
| | | | | Test A: | Test B: |
| | Glu(−) St % (g/g) | Glu(+) Lb % (g/g) | Ratio of St to Lb | Cell count Lb (CFU/g) | Cell count Lb (CFU/g) |
| 1 | 94.0 | 6.0 | 119.32 | 1.9E08 | 2.0E08 |
| | | | | 1.9E08 | 2.0E08 |
| 2 | 94.5 | 5.5 | 130.86 | 1.9E08 | 1.9E08 |
| | | | | 2.0E08 | 1.9E08 |
| 3 | 95.0 | 5.0 | 144.71 | 1.9E08 | 1.8E08 |
| | | | | 1.9E08 | 1.9E08 |
| 4 | 95.5 | 4.5 | 161.64 | 1.7E08 | 1.7E08 |
| | | | | 1.7E08 | 1.8E08 |
| 5 | 96.0 | 4.0 | 182.79 | 1.5E08 | 1.7E08 |
| | | | | 1.6E08 | 1.6E08 |
| 6 | 96.5 | 3.5 | 210.00 | 1.7E08 | 1.6E08 |
| | | | | 1.7E08 | 1.6E08 |
| 7 | 97.0 | 3.0 | 246.26 | 1.8E08 | 1.7E08 |
| | | | | 1.7E08 | 1.8E08 |
| 8 | 97.5 | 2.5 | 297.04 | 1.4E08 | 1.7E08 |
| | | | | 1.4E08 | 1.7E08 |
| 9 | 98.0 | 2.0 | 373.20 | 2.1E08 | 1.7E08 |
| | | | | 1.9E08 | 1.6E08 |
| 10 | 98.5 | 1.5 | 500.14 | 1.3E08 | 1.6E08 |
| | | | | 1.1E08 | 1.5E08 |
| 11 | 99.0 | 1.0 | 754.02 | 1.0E08 | 1.5E08 |
| | | | | 8.9E07 | 1.5E08 |
| 12 | 99.5 | 0.5 | 1515.66 | 7.0E07 | 1.3E08 |
| | | | | 6.7E07 | 1.2E08 |

Glu(−): Glucose-deficient
Glu(+): Glucose-positive
St: *Streptococcus thermophilus*
Lb: *Lactobacillus delbrueckii* subsp. *bulgaricus*

Two tests A and B were carried out to obtain a double, independent determination. In each test A and B, replicate determinations for each blend were carried out, and the cell count (CFU/g) was determined at the end of the fermentation. The results will appear from Table 2. As will appear from the results, the cell count for *Lactobacillus delbrueckii* subsp. *bulgaricus* at the end of the fermentation was at a very high level, i.e. between 6.7E07 and 2.1E08, for all blends. Furthermore, reducing the level of *Lactobacillus delbrueckii* subsp. *bulgaricus* in relation to the sum of the glucose-deficient *Streptococcus thermophilus* strains in the blends used for inoculation had very little effect on the cell count for *Lactobacillus delbrueckii* subsp. *bulgaricus* at the end of the fermentation for most blends. Thus, for ratios of *Streptococcus thermophilus* to *Lactobacillus delbrueckii* subsp. *bulgaricus* from 119.32 to 373.20, the Lb cell count after fermentation was at the same high level of between 1.4E08 to 2.1E08. For ratios of St to Lb from 500.14 to 1515.66 the Lb cell count after fermentation was at a slightly lower level of between 6.7E07 to 1.6E08, which is a surprisingly high level considering the extremely low level of Lb in the inoculation blend. Also, the said level of Lb cell count obtained after fermentation of between 6.7E07 to 1.6E08 is significantly higher than the level obtained with glucose-positive strains, cf. Comparative Example 3.

Thus, the present experiment has shown that glucose-deficient *Streptococcus thermophilus* strains increase the growth of *Lactobacillus delbrueckii* subsp. *bulgaricus* to a high degree and independently of the initial level of *Lactobacillus delbrueckii* subsp. *bulgaricus*.

Comparative Example 3: Effect of Glucose-Positive *Streptococcus thermophilus* Strains on the Growth of *Lactobacillus* Strains in Fermentation of Milk Using Low *Lactobacillus* Cell Counts For the purpose of comparison with the results of Example 2, bacteria strain blends in different ratios of a mixture of glucose-positive *Streptococcus thermophilus* strains to a glucose-positive *Lactobacillus delbrueckii* subsp. *bulgaricus* strain were tested in a process of producing yogurt from a milk substrate in order to determine the effect of glucose-deficient *Streptococcus thermophilus* strains on the growth of *Lactobacillus delbrueckii* subsp. *bulgaricus* strains. The composition of the said blends and the said different ratios appear from Table 3.

The fermentations were carried out using the same process and conditions as specified in Example 2.

TABLE 3

Growth of *Lactobacillus delbrueckii* subsp. *bulgaricus* in the presence of glucose-positive *Streptococcus thermophilus* at different ratios

| | Culture composition | | | Lb cell count after fermentation | |
|---|---|---|---|---|---|
| | Glu(+) St % (g/g) | Glu(+) Lb % (g/g) | Ratio of St to Lb | Test A: Cell count Lb (CFU/g) | Test B: Cell count Lb (CFU/g) |
| 1 | 94.0 | 6.0 | 97.85 | 1.6E07 / 1.6E07 | 1.5E07 / 1.5E07 |
| 2 | 94.5 | 5.5 | 107.31 | 1.0E07 / 9.5E06 | 1.2E07 / 1.1E07 |
| 3 | 95.0 | 5.0 | 118.67 | 9.4E06 / 9.0E06 | 1.0E07 / 1.1E07 |
| 4 | 95.5 | 4.5 | 132.55 | 8.4E06 / 8.4E06 | 9.0E06 / 8.7E06 |
| 5 | 96.0 | 4.0 | 149.90 | 6.9E06 / 7.2E06 | 7.5E06 / 7.4E06 |
| 6 | 96.5 | 3.5 | 172.20 | 7.0E06 / 7.4E06 | 7.3E06 / 7.6E06 |
| 7 | 97.0 | 3.0 | 201.94 | 6.5E06 / 6.8E06 | 6.1E06 / 6.5E06 |
| 8 | 97.5 | 2.5 | 243.58 | 5.8E06 / 5.8E06 | 6.4E06 / 6.4E06 |
| 9 | 98.0 | 2.0 | 306.04 | 4.4E06 / 4.7E06 | 5.2E06 / 4.9E06 |
| 10 | 98.5 | 1.5 | 410.13 | 2.8E06 / 3.2E06 | 4.2E06 / 4.6E06 |
| 11 | 99.0 | 1.0 | 618.32 | 2.4E06 / 2.8E06 | 3.1E06 / 3.3E06 |
| 12 | 99.5 | 0.5 | 1242.89 | 2.1E06 / 2.3E06 | 2.8E06 / 2.7E06 |

Glu(−): Glucose-deficient
Glu(+): Glucose-positive
St: *Streptococcus thermophilus*
Lb: *Lactobacillus delbrueckii* subsp. *bulgaricus*

Two tests A and B were carried out to obtain a double, independent determination. In each test A and B, replicate determinations for each blend were carried out, and the cell count (CFU/g) was determined at the end of the fermentation. The results will appear from Table 3. As will appear from the results, the cell count for *Lactobacillus delbrueckii* subsp. *bulgaricus* at the end of the fermentation was at a moderate level of between 2.1E06 and 1.6E07. Furthermore, low levels of *Lactobacillus delbrueckii* subsp. *bulgaricus* relative to the sum of the glucose-positive *Streptococcus thermophilus* strains in the blends used for inoculation apparently causes a significantly stronger reduction in the cell count for *Lactobacillus delbrueckii* subsp. *bulgaricus* obtained at the end of the fermentation than is the case for the glucose-deficient *Streptococcus thermophilus* strains, cf. Example 2. Thus, the results of the present experiments confirm that glucose-deficient *Streptococcus thermophilus* strains increase the growth of *Lactobacillus delbrueckii* subsp. *bulgaricus* significantly as compared to glucose-positive *Streptococcus thermophilus* strains.

Example 4: Effect of Glucose-Deficient *Streptococcus thermophilus* Strains on the Growth of *Lactobacillus acidophilus* and *Lactobacillus paracasei* Strains in Fermentation of Milk Composition of Inoculation Cultures

TABLE 4

Composition of reference culture blends

| | La % (g/g) | Lc % (g/g) | Glu(+) St % (g/g) | Glu(+) Lb % (g/g) |
|---|---|---|---|---|
| Ref. 1: La high + Lb + St Blend 1 | 32.0 | | 64.0 | 4.0 |
| Ref. 2: Lc high + Lb + St Blend 1 | | 32.0 | 64.0 | 4.0 |
| Ref. 3: La high + Lb + St Blend 2 | 31.6 | | 61.3 | 7.1 |
| Ref. 4: Lc high + Lb + St Blend 2 | | 31.6 | 61.3 | 7.1 |
| Ref. 5: La low + lb + St Blend 1 | 8.2 | | 86.8 | 5.0 |
| Ref. 6: Lc low + lb + St Blend 1 | | 8.2 | 86.8 | 5.0 |
| Ref. 7: La low + Lb + St Blend 2 | 8.5 | | 82.0 | 9.5 |
| Ref. 8: Lc low + Lb + St Blend 2 | | 8.5 | 82.0 | 9.5 |

La: *Lactobacillus acidophilus*, LA-5, CHCC2169.
Lc: *Lactobacillus paracasei*, LC-01, CHCC2115.
Glu(+): Glucose-positive
St: *Streptococcus thermophilus*
Lb: *Lactobacillus delbrueckii* subsp. *bulgaricus*
St Blend 1 contains two glucose-positive St strains.
St Blend 2 contains three gluocse-positive St strains.

TABLE 5

Composition of culture blends according to the present invention

| | La % (g/g) | Lc % (g/g) | Glu(−) St % (g/g) | Glu(−) Lb % (g/g) |
|---|---|---|---|---|
| 1: La high + Lb + St Blend 3 | 31.7 | | 62.7 | 5.6 |
| 2: Lc high + Lb + St Blend 3 | | 31.7 | 62.7 | 5.6 |
| 3: La low + Lb + St Blend 3 | 8.5 | | 84.0 | 7.5 |
| 4: Lc low + Lb + St Blend 3 | | 8.5 | 84.0 | 7.5 |

La: *Lactobacillus acidophilus*, LA-5, CHCC2169.
Lc: *Lactobacillus paracasei*, LC-01, CHCC2115.
Glu(−): Glucose-deficient
St: *Streptococcus thermophilus*
Lb: *Lactobacillus delbrueckii* subsp. *bulgaricus*
St Blend 3 contains three glucose-deficient St strains.
0.05% sucrose was added to all fermentations using glucose-deficient St.

Analysis
1. Acidification curves during fermentation (not shown)
2. Cell count at the end of fermentation
3. Day 1: pH and cell count. Storage at 6° C.
4. Day 14: pH and cell count. Storage at 6° C.
5. Day 28: pH and cell count. Storage at 6° C.
6. Day 42: pH and cell count. Storage at 6° C.

Acidification curves were measured by a Cinac system (by Alliance Instruments, an AMS Company Brand).

All fermentations were carried out in two replicates.

The fermentations were carried out in 9.5% B-milk (milk substrate).

Cell counts were carried out by plating on Petri dishes using standardized agar medium adapted for growth of the *Lactobacillus acidophilus* strain and the *Lactobacillus paracasei* strain. The method described above under Methods and Materials for *Lactobacillus delbrueckii* subsp. *bulgaricus* strains was used.

Results Post-Acidification

TABLE 6 pH for reference culture blends

| pH | Day 1 | Day 14 | Day 28 |
| --- | --- | --- | --- |
| Ref. 1: La high + Lb + St Blend 1 | 4.50 | 4.35 | 4.35 |
| Ref. 2: Lc high + Lb + St Blend 1 | 4.49 | 4.35 | 4.35 |
| Ref. 3: La high + Lb + St Blend 2 | 4.49 | 4.34 | 4.33 |

TABLE 6-continued pH for reference culture blends

| pH | Day 1 | Day 14 | Day 28 |
| --- | --- | --- | --- |
| Ref. 4: Lc high + Lb + St Blend 2 | 4.50 | 4.34 | 4.34 |
| Ref. 5: La low + lb + St Blend 1 | 4.48 | 4.35 | 4.35 |
| Ref. 6: Lc low + lb + St Blend 1 | 4.49 | 4.35 | 4.36 |
| Ref. 7: La low + Lb + St Blend 2 | 4.49 | 4.36 | 4.33 |
| Ref. 8: Lc low + Lb + St Blend 2 | 4.48 | 4.35 | 4.33 |

TABLE 7 pH of culture blends according to the present invention

| pH | Day 1 | Day 14 | Day 28 |
| --- | --- | --- | --- |
| 1: La high + Lb + St Blend 3 | 4.51 | 4.35 | 4.37 |
| 2: Lc high + Lb + St Blend 3 | 4.49 | 4.35 | 4.35 |
| 3: La low + Lb + St Blend 3 | 4.48 | 4.35 | 4.35 |
| 4: Lc low + Lb + St Blend 3 | 4.49 | 4.35 | 4.36 |

Results Cell Counts

TABLE 8

Cell counts for reference culture blends

| CFU/g | Day 1 | | Day 14 | | Day 42 | |
| --- | --- | --- | --- | --- | --- | --- |
| La count for Ref. 1: La high + Lb + St Blend 1 | 5.8E06 | 4.9E06 | 7.6E06 | 6.6E06 | 1.7E06 | 2.8E06 |
| Lc count for Ref. 2: Lc high + Lb + St Blend 1 | 1.2E06 | 2.8E06 | 8.4E05 | 7.7E05 | 7.0E05 | 1.7E06 |
| La count for Ref. 3: La high + Lb + St Blend 2 | 6.4E06 | 5.2E06 | 8.2E06 | 6.4E06 | 3.4E06 | 1.05E06 |
| Lc count for Ref. 4: Lc high + Lb + St Blend 2 | 3.0E06 | 1.6E06 | 2.1E06 | 2.1E06 | 2.1E06 | 1.8E06 |
| La count for Ref. 5: La low + lb + St Blend 1 | 2.5E06 | 2.1E06 | 2.57E06 | 2.6E06 | 1.5E06 | 1.5E06 |
| Lc count for Ref. 6: Lc low + lb + St Blend 1 | 1.0E06 | 8.0E05 | 6.7E05 | 2.8E05 | 5.0E05 | 2.5E05 |
| La count for Ref. 7: La low + Lb + St Blend 2 | 9.2E05 | 2.7E06 | 1.05E06 | 1.6E06 | 3.5E05 | 2.1E05 |
| Lc count for Ref. 8: Lc low + Lb + St Blend 2 | 1.4E06 | 1.3E05 | 5.4E05 | 4.0E04 | ND | 1.8E04 |

ND: No data

TABLE 9

Cell counts for culture blends according to the present invention

| CFU/g | Day 3 | | Day 14 | |
|---|---|---|---|---|
| La count for 1:<br>La high + Lb + St<br>Blend 3 | 1.6E07 | 3.2E07 | 6.6E06 | 1.7E07 |
| Lc count for 2:<br>Lc high + Lb + St<br>Blend 3 | 2.3E07 | 6.3E07 | 3.8E07 | 3.4E07 |
| La count for 3:<br>La low + Lb + St<br>Blend 3 | 8.0E06 | 8.3E06 | 6.5E05 | ND |
| Lc count for 4:<br>Lc low + Lb + St<br>Blend 3 | 1.2E07 | 1.5E07 | 9.5E06 | 1.0E07 |

ND: No data

Discussion of results

Culture blend 1 of the invention is compared to references 1 and 3.

Culture blend 2 of the invention is compared to references 2 and 4.

Culture blend 3 of the invention is compared to references 5 and 7.

Culture blend 4 of the invention is compared to references 6 and 8.

As will appear from Tables 8 and 9, the glucose-deficient *Streptococcus thermophilus* blend (St blend 3 of Tables 8 and 9) enhanced the cell count (see Day 3) of both the *Lactobacillus acidophilus* strain and the *Lactobacillus paracasei* strain (see Day 1). The cell count is enhanced for both a low and a high level of the *Lactobacillus acidophilus* strain or the *Lactobacillus paracasei* strain in the culture blend inoculated to the milk substrate. The enhancement in cell count had an order of magnitude of from about one half to about one and a half logarithmic orders.

Deposits and Expert Solutions

The applicant requests that a sample of the deposited micro-organisms stated below may only be made available to an expert, until the date on which the patent is granted.

The strain *Streptococcus thermophilus* CHCC19216 has been deposited at Deutsche Sammlung von Mikroorganismen und Zellkulturen (DSMZ) GmbH, Inhoffenstr. 7B, D-38124 Braunschweig, Germany, on 8 Dec. 2015 under the accession No. DSM 32227.

The strain *Streptococcus thermophilus* CHCC16731 has been deposited at Deutsche Sammlung von Mikroorganismen und Zellkulturen (DSMZ) GmbH, Inhoffenstr. 7B, D-38124 Braunschweig, Germany, on 4 Jun. 2014 under the accession No. DSM 28889.

The strain *Streptococcus thermophilus* CHCC15757 has been deposited at Deutsche Sammlung von Mikroorganismen und Zellkulturen (DSMZ) GmbH, Inhoffenstr. 7B, D-38124 Braunschweig, Germany, on 3 Apr. 2012 under the accession No. DSM 25850

The strain *Streptococcus thermophilus* CHCC15887 has been deposited at Deutsche Sammlung von Mikroorganismen und Zellkulturen (DSMZ) GmbH, Inhoffenstr. 7B, D-38124 Braunschweig, Germany, on 3 Apr. 2012 under the accession No. DSM 25851

The strain *Streptococcus thermophilus* CHCC16404 has been deposited at Deutsche Sammlung von Mikroorganismen und Zellkulturen (DSMZ) GmbH, Inhoffenstr. 7B, D-38124 Braunschweig, Germany, on 12 Dec. 2012 under the accession No. DSM 26722.

The strain *Streptococcus thermophilus* CHCC14994 has been deposited at Deutsche Sammlung von Mikroorganismen und Zellkulturen (DSMZ) GmbH, Inhoffenstr. 7B, D-38124 Braunschweig, Germany, on 3 Apr. 2012 under the accession No. DSM 25838.

The strain *Streptococcus thermophilus* CHCC11976 has been deposited at Deutsche Sammlung von Mikroorganismen und Zellkulturen (DSMZ) GmbH, Inhoffenstr. 7B, D-38124 Braunschweig, Germany, on 8 Sep. 2009 under the accession No. DSM 22934.

The strain *Lactobacillus delbrueckii* subsp. *bulgaricus* CHCC759 has been deposited at Deutsche Sammlung von Mikroorganismen und Zellkulturen (DSMZ) GmbH, Inhoffenstr. 7B, D-38124 Braunschweig, Germany, on 6 Sep. 2012 under the accession No. DSM 26419.

The strain *Lactobacillus delbrueckii* subsp. *bulgaricus* CHCC10019 has been deposited at Deutsche Sammlung von Mikroorganismen und Zellkulturen (DSMZ) GmbH, Inhoffenstr. 7B, D-38124 Braunschweig, Germany, on 3 Apr. 2007 under the accession No. DSM 19252.

The strain *Lactobacillus delbrueckii* subsp. *bulgaricus* CHCC16159 has been deposited at Deutsche Sammlung von Mikroorganismen und Zellkulturen (DSMZ) GmbH, Inhoffenstr. 7B, D-38124 Braunschweig, Germany, on 6 Sep. 2012 under the accession No. DSM 26420.

The strain *Lactobacillus delbrueckii* subsp. *bulgaricus* CHCC16160 has been deposited at Deutsche Sammlung von Mikroorganismen und Zellkulturen (DSMZ) GmbH, Inhoffenstr. 7B, D-38124 Braunschweig, Germany, on 6 Sep. 2012 under the accession No. DSM 26421.

The strain *Lactobacillus delbrueckii* subsp. *bulgaricus* CHCC4351 has been deposited at Deutsche Sammlung von Mikroorganismen und Zellkulturen (DSMZ) GmbH, Inhoffenstr. 7B, D-38124 Braunschweig, Germany, on 19 May 2009 under the accession No. DSM 22586.

The strain *Lactobacillus acidophilus* La-5, CHCC2169, has been deposited as DSM13241 on 2003-09-30 at Deutsche Sammlung von Mikroorganismen und Zellkulturen GmbH Maschroder Weg 1b, D-38124 Braunschweig.

The strain *Lactobacillus paracasei* CHCC2115, LC-01, was deposited with DSMZ-Deutsche Sammlung von Mikroorganismen und Zellkulturen GmbH, Inhoffenstr. 7B, D-38124 Braunschweig. Germany, on 27 Jun. 2007 under the accession no. DSM 19465.

The deposits were made according to the Budapest treaty on the international recognition of the deposit of microorganisms for the purposes of patent procedure.

REFERENCES

WO 2011/026863

Pool et al. (2006) Metabolic Engineering 8(5); 456-464

Cochu et al. (2003). Appl. and Environ Microbiol., 69(9), 5423-5432

Høier et al. (2010) in The Technology of Cheesemaking, $2^{nd}$ Ed. Blackwell Publishing, Oxford; 166-192.

The invention claimed is:

1. A process for improving growth of a *Lactobacillus* strain in a process for producing a fermented milk product, comprising inoculating and fermenting a milk substrate with a *Lactobacillus* strain and a glucose-deficient *Streptococcus thermophilus* strain, wherein the *Streptococcus thermophilus* strain improves growth of the *Lactobacillus* strain as determined by an increased cell count of the *Lactobacillus* strain when fermented with the glucose-deficient *Streptococcus thermophilus* strain as compared to fermentation with a glucose-positive *Streptococcus thermophilus* strain.

2. The process of claim 1, wherein the *Streptococcus thermophilus* strain is galactose-fermenting and carries a mutation in the DNA sequence of a glcK gene encoding a glucokinase protein, wherein the mutation inactivates the glucokinase protein or has a negative effect on expression of the glcK gene.

3. The process of claim 1, wherein the *Streptococcus thermophilus* strain carries a mutation that reduces transport of glucose into a cell.

4. The process of claim 3, wherein the *Streptococcus thermophilus* strain carries a mutation in a gene encoding a component of a glucose transporter, wherein the mutation inactivates the glucose transporter or has a negative effect on expression of the gene encoding a component of a glucose transporter.

5. The process of claim 4, wherein the *Streptococcus thermophilus* strain carries a mutation in the DNA sequence of a manM gene encoding a $IIC^{Man}$ protein of a glucose/mannose phosphotransferase system, wherein the mutation inactivates the $IIC^{Man}$ protein or has a negative effect on expression of the manM gene.

6. The process of claim 1, wherein the *Streptococcus thermophilus* strain increases the amount of glucose in 9.5% B-milk to at least 5 mg/ml when inoculated into the 9.5% B-milk at a concentration of $1.0 \times 10^6$-$1.0 \times 10^7$ CFU/ml and grown at 40° C. for 20 hours, wherein the 9.5% B-milk is heat-treated milk made with low fat skim milk powder reconstituted to a level of dry matter of 9.5% and pasteurized at 99° C. for 30 minutes followed by cooling to 40° C.

7. The process of claim 1, wherein the *Streptococcus thermophilus* strain is a deposited strain selected from *Streptococcus thermophilus* strain CHCC15757 deposited at Deutsche Sammlung von Mikroorganismen und Zellkulturen (DSMZ) under Accession No. DSM 25850, the *Streptococcus thermophilus* strain CHCC15887 deposited at DSMZ under Accession No. DSM 25851, the *Streptococcus thermophilus* strain CHCC16404 deposited at DSMZ under Accession No. DSM 26722, the *Streptococcus thermophilus* strain CHCC16731 deposited at DSMZ under Accession No. DSM 28889, the *Streptococcus thermophilus* strain CHCC19216 deposited with DSMX under Accession No. DSM 32227, and mutant strains derived therefrom, wherein the mutant strains are obtained by using one of the deposited strains as starting material, and wherein the mutant strains have a retained or further improved glucose secreting property as compared to the deposited strain used as starting material.

8. The process of claim 1, wherein the *Lactobacillus* strain is selected from *Lactobacillus delbrueckii, Lactobacillus delbrueckii* subsp. *bulgaricus, Lactobacillus delbrueckii* subsp. *lactis, Lactobacillus paracasei, Lactobacillus casei, Lactobacillus rhamnosus, Lactobacillus fermentum, Lactobacillus plantarum, Lactobacillus helveticus*, and *Lactobacillus acidophilus*.

9. The process of claim 1, wherein the *Lactobacillus* strain is a *Lactobacillus delbrueckii* subsp. *bulgaricus* strain.

10. The process of claim 9, wherein the *Lactobacillus delbrueckii* subsp. *bulgaricus* strain is a deposited strain selected from the *Lactobacillus delbrueckii* subsp. *bulgaricus* strain CHCC16159 deposited at DSMZ under Accession No. DSM 26420, the *Lactobacillus delbrueckii* subsp. *bulgaricus* strain CHCC16160 deposited at DSMZ under Accession No. DSM 26421, and mutant strains derived therefrom, wherein the mutant strains are obtained by using one of the deposited strains as starting material, and wherein the mutant strains have a retained or further improved glucose secreting property as compared to the deposited strain used as starting material.

11. The process of claim 1, wherein the *Streptococcus thermophilus* strain increases the cell count of the *Lactobacillus* strain to at least $5.0 \times 10^6$ CFU/g in the fermented milk product at end of fermentation, when the *Streptococcus thermophilus* strain is inoculated into the milk substrate at a concentration of $1.0 \times 10^7$- $1.0 \times 10^8$ CFU/g and grown at 43° C. until the pH reaches 4.55, wherein the milk substrate is a mixture of fresh skimmed milk with a fat content of 0.1%, fresh semi-skimmed milk with a fat content of 1.5%, and skimmed milk powder, and wherein the milk substrate contains 4.7% protein and 1.0% fat, and 0.05% sucrose.

12. The process of claim 1, wherein at the start of the fermentation the ratio of *Streptococcus thermophilus* strain in CFU/g to *Lactobacillus* strain in CFU/g is at least 50.

* * * * *